United States Patent [19]

Matsumoto

[11] Patent Number: 5,204,268
[45] Date of Patent: Apr. 20, 1993

[54] METHOD AND APPARATUS FOR APPLYING LIQUID SAMPLES

[75] Inventor: Masaki Matsumoto, Kanagawa, Japan

[73] Assignee: Fuji Photo Film Co., Ltd., Kanagawa, Japan

[21] Appl. No.: 825,843

[22] Filed: Jan. 28, 1992

Related U.S. Application Data

[63] Continuation of Ser. No. 360,636, Jun. 2, 1989, abandoned.

[30] Foreign Application Priority Data

Jun. 2, 1988 [JP] Japan .................. 63-136002

[51] Int. Cl.$^5$ .................. G01N 35/00; G01N 21/01
[52] U.S. Cl. .................. 436/44; 436/46; 436/47; 436/49; 436/50; 422/66; 422/67; 422/100
[58] Field of Search .................. 422/56, 63, 66, 67, 422/82.05, 82.06, 100, 102; 436/44, 46-51

[56] References Cited

U.S. PATENT DOCUMENTS

| | | | |
|---|---|---|---|
| 3,526,480 | 9/1970 | Findl et al. | 435/4 X |
| 3,728,081 | 4/1973 | Bidanset | 422/66 |
| 4,276,260 | 6/1981 | Orbal et al. | 422/63 X |
| 4,340,390 | 7/1982 | Collins et al. | 422/63 X |
| 4,495,149 | 1/1985 | Iwata et al. | 436/49 X |
| 4,715,413 | 12/1987 | Backlund et al. | 422/100 X |
| 4,857,272 | 8/1989 | Sugaya | 422/65 |
| 4,944,922 | 7/1990 | Hayashi | 422/107 X |
| 5,049,359 | 9/1991 | Azuma et al. | 436/46 X |
| 5,102,624 | 4/1992 | Muraishi | 422/64 |

Primary Examiner—James C. Housel
Assistant Examiner—Arlen Soderquist
Attorney, Agent, or Firm—Sughrue, Mion, Zinn Macpeak & Seas

[57] ABSTRACT

A method for applying a droplet of a liquid sample from a sample applying nozzle, which is movable between a retracted position and a sample applying position, to a test film which contains a reagent which will react with a liquid sample and give rise to a change in optical density, includes providing the leading edge of the sample applying nozzle with a test film sensor. Prior to the application of the droplet of the liquid sample to the test film, the sample applying nozzle is moved down until the test film sensor comes into contact with the test film, and the distance by which the sample applying nozzle was moved down is stored. At the time the liquid sample is applied to the test film, the distance by which the sample applying nozzle is moved down is adjusted in accordance with the stored distance so that the sample applying nozzle is moved down to a sample applying position spaced a predetermined distance from the test film.

3 Claims, 5 Drawing Sheets

METHOD AND APPARATUS FOR APPLYING LIQUID SAMPLES

This is a continuation of application Ser. No. 07/360,636 filed Jun. 2, 1989, now abandoned.

BACKGROUND OF THE INVENTION

1. Field of the Invention

This invention relates to a method for accurately applying liquid samples in a biochemical analysis process, and a device for carrying out the method.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

Recently, as disclosed in, for example, Japanese Patent Publication No. 53(1978)-21677 and Japanese Unexamined Patent Publication No. 55(1980)-164356, a dry type chemical analysis slide was developed for use in a system designed for performing quantitative analyses, with which system the amount of a specific chemical constituent or a specific physical constituent contained in a droplet of a liquid sample, which is simply applied to a slide, is determined. It is possible to analyze a liquid sample more simply and more accurately with methods in which a chemical analysis slide is used than with methods in which a conventional wet type analysis is carried out. Therefore, it is desirable to use chemical analysis slides, particularly in medical organizations, research laboratories, or the like where many samples must be analyzed.

In order to use a chemical analysis slide in the analysis of a chemical constituent or the like contained in a liquid sample, a measured amount of the liquid sample is put on the chemical analysis slide and is kept at a predetermined temperature (i.e. incubated) for a predetermined time in an incubator, which causes a color reaction. The chemical analysis slide is then exposed to light having a wavelength which is selected in advance, the selection of which wavelength depends on the constituents of the liquid sample and the constituents of a reagent contained in the reagent layer in the chemical analysis slide. Quantitative analysis of a chemical constituent or the like in a sample is carried out by irradiating a reaction product which forms on the chemical analysis slide with light and finding the ratio of transmitted vs. reflected light.

In medical organizations, research laboratories or the like where many liquid samples are analyzed, it is desirable to conduct analyses automatically and sequentially. To satisfy this need, various chemical analysis apparatuses have been proposed, which use the aforesaid chemical analysis slides. One such chemical analysis apparatus is disclosed in, for example, Japanese Unexamined Patent Publication No. 56(1981)-77746. Also, as a means with which liquid samples can be automatically and sequentially analyzed, an apparatus is proposed in, for example, U.S. Pat. No. 3,526,480, in which apparatus a long tape-like test film containing a reagent is used instead of the aforesaid chemical analysis slides, and the application, incubation and measurement of samples are carried out sequentially on adjacent portions of the test film. The operating cost of an apparatus using a long tape-like test film is lower than the operating cost of an apparatus using chemical analysis slides, and a simple mechanism makes it possible for measurements on many liquid samples to be carried out sequentially.

The chemical analysis slides and the long test film will hereinbelow be generically referred to as the test film. In biochemical analysis apparatuses having the configuration described above, a special device is employed with which liquid samples are applied to the test film. With the device for applying liquid samples, a liquid sample is accommodated in a sample applying nozzle and is delivered therefrom until a droplet of the liquid sample forms at the leading edge of the sample applying nozzle. The sample applying nozzle is then moved down until the droplet comes into contact with the test film. The droplet is thus applied to the test film with the aid of surface tension. The method for applying liquid samples, wherein a droplet of a liquid sample forms at the leading edge of a sample applying nozzle instead of being jetted out of the sample applying nozzle, is suitable for biochemical analysis processes wherein only very small amounts (for example, approximately 4 $\mu$l) of the liquid samples are available.

In order to accurately to apply liquid samples to the test film with the aforesaid type of device for applying liquid samples, it is necessary that the distance between the leading edge of the sample applying nozzle and the surface of the test film, to which surface a liquid sample is to be applied, be always constant at the time of sample application. However, test films containing different reagents are used in accordance with the types of the constituents in the liquid samples which are to be subjected to measurement. The thickness of the test films often differs depending on the types of reagents contained in the test films. Therefore, if the position of the leading edge of the sample applying nozzle is constant during sample application, a sample application may not be carried out accurately depending on the type of test film used. Such problems occur in multi-channel type devices wherein a plurality of test films containing different reagents are accommodated, to which test films liquid samples are sequentially applied, and in single-channel type devices wherein a plurality of test films containing different reagents are sequentially used.

Also, in multi-channel type devices, the height at which each test film is supported fluctuates because of fluctuations in the dimensional accuracy of a plurality of supporting means which support the test films. In such cases, the distance between the sample applying nozzle and the surface of each test film, to which surface a liquid sample is to be applied, changes.

SUMMARY OF THE INVENTION

The primary object of the present invention is to provide a method for applying liquid samples wherein liquid samples ar applied accurately even though the heights of the surfaces of test films, to which surfaces liquid samples are to be applied, vary.

Another object of the present invention is to provide a device for carrying out the method.

The present invention provides a method for applying liquid samples in which a liquid sample accommodated in a sample applying nozzle is delivered therefrom until a droplet of the liquid sample forms at the leading edge of the sample applying nozzle, the sample applying nozzle is then moved down to a sample applying position slightly above a test film, which contains a reagent which will react with the liquid sample and give rise to a change in optical density, so that the droplet comes into contact with the test film and is applied thereto, wherein the improvement comprises the steps of:

i) providing the leading edge of said sample applying nozzle with a test film sensor, ii) moving said sample applying nozzle down prior to the formation and application of the droplet of said liquid sample until said test film sensor comes into contact with said test film, iii) storing the distance by which said sample applying nozzle was moved down, and iv) at the time said liquid sample is applied to said test film adjusting the distance by which said sample applying nozzle is moved down in accordance with said stored distance so that said sample applying nozzle is moved down to a sample applying position spaced a predetermined distance from said test film.

The present invention also provides a device for applying liquid samples which comprises a supporting means for supporting a test film which contains a reagent, which will react with a liquid sample and give rise to a change in optical density, a sample applying nozzle capable of accommodating the liquid sample and delivering it in such a way that a droplet thereof forms at the leading edge of the sample applying nozzle, and a vertical movement means for vertically moving the sample applying nozzle between a sample applying position close to the test film and a retracted position above said sample applying position, wherein the improvement comprises the provision of:

i) a test film sensor provided at the leading edge of said sample applying nozzle, ii) a storage means for storing the distance by which said sample applying nozzle is moved down by said vertical movement means from said retracted position until said test film sensor comes into contact with said test film, and iii) a control means for adjusting the distance, by which said sample applying nozzle is moved down from said retracted position to said sample applying position, in accordance with said stored distance.

With the method and device for applying liquid samples in accordance with the present invention, before a droplet of the liquid sample forms at the leading edge of the sample applying nozzle and is applied to the test film, the position of the test film is detected by the test film sensor provided at the leading edge of the sample applying nozzle. When the liquid sample is applied to the test film the distance by which the sample applying nozzle is moved down is adjusted in accordance with the detected position of the test film so that the sample applying position of the sample applying nozzle is spaced a predetermined distance from the test film. Therefore, liquid samples can be applied accurately even though the heights of the surfaces of test films, to which surfaces liquid samples are to be applied, vary because of fluctuations in the thickness of the test films and/or the heights at which the test films are supported.

DESCRIPTION OF THE PREFERRED EMBODIMENTS

The present invention will hereinbelow be described in further detail with reference to the accompanying drawings.

Figure 1:
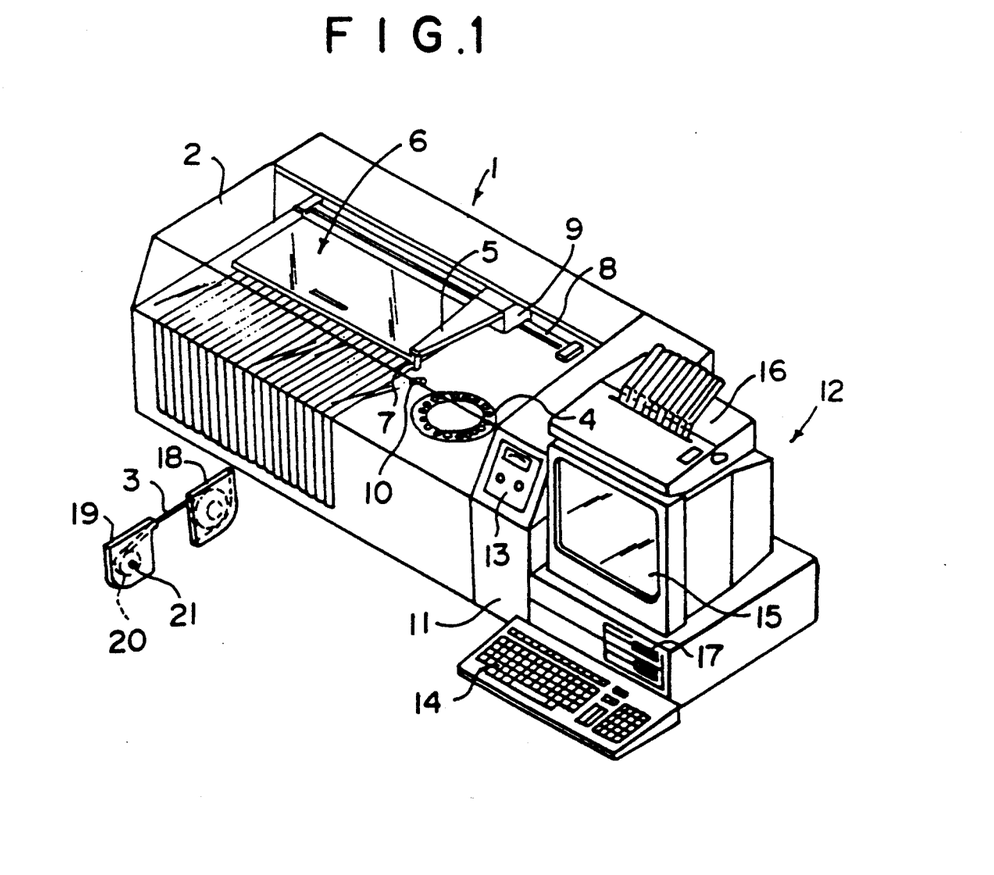
FIG. 1 is a perspective view showing a biochemical analysis apparatus wherein an embodiment of the device for applying liquid samples in accordance with the present invention is employed.

With reference to FIG. 1, a biochemical analysis apparatus 1 is provided with a transparent cover 2. The cover 2 is opened when a liquid sample, a long tape-like test film 3 or the like are fed into and out of the apparatus 1. The apparatus 1 is provided with a sample accommodating means 4 which is a ring-like structure for accommodating liquid samples such as blood serum or urine, and a liquid sample is taken up from the sample accommodating means 4 by a sample application arm 5 provided with a sample applying nozzle 7 as will be described later. The liquid sample is applied from the sample applying nozzle 7 onto the long test film 3. The long test film 3 contains a reagent that undergoes a color reaction only with the specific chemical constituent (or the specific physical constituent) of the liquid sample that is to be analyzed, and many kinds of long test films 3 are prepared depending on what the specific chemical constituent to be analyzed is. The portion of the long test film 3 which has not yet been used in an analysis of a liquid sample is wound up in a film feed cassette 18, and the portion of the long test film 3 which has already been used for measurement is wound up in a film wind-up cassette 19. At the center of a reel 20 in the film wind-up cassette 19, a hole 21 is provided with which a rotation shaft of a motor engages, which motor pulls the long test film 3 out of the film feed cassette 18 after the long test film 3 has been accommodated in the biochemical analysis apparatus 1 as will be described later. The long test film 3 is accommodated in the biochemical analysis apparatus 1 and is wound up in the film feed cassette 18 and the film wind-up cassette 19. As shown in FIG. 1, the film feed cassette 18 and the film wind-up cassette 19 are formed independently of each other. A test film accommodating means 6 accommodates unused portions of a plurality of long test films 3 in parallel, which allows the apparatus 1 to be used in the simultaneous analysis of various different constituents in liquid samples.

The sample application arm 5 is provided with the sample applying nozzle 7 at its end, and is moved along a rail 8 by a movement means 9 placed on the rail 8. The sample applying nozzle 7 takes up the liquid sample from the sample accommodating means 4, and applies the liquid sample to a portion of the long test film 3 which portion has been pulled out of the test film accommodating means 6 in a manner which will be described later. The movement means 9 is provided with a vertical movement means which moves the sample application arm 5 vertically. The sample application arm 5 is kept in a retracted position (upper position)

during the time it is being moved by the movement means 9 along the rail 8, and is moved down to a sample applying position during the times it is taking a liquid sample out of the sample accommodating means 4 and applying a liquid sample to the long test film 3, and during the time it is being washed as will be described later.

After applying the liquid sample to the test film, the sample applying nozzle 7 is washed at a nozzle washing area 10 provided between the test film accommodating means 6 and the sample accommodating means 4. The washed sample applying nozzle 7 is then later reused in another application of a sample.

The test film to which the liquid sample has already been applied is incubated by an incubator as will be described later and subjected to being measured by a density measuring device.

Control of the operation of the overall apparatus 1, the processing of data obtained from the analysis of a liquid sample and the like are carried out by an electronic processing circuit means 11 and a computer 12 connected thereto. An operating and display means 13 on the front surface of the electronic processing circuit means 11 is provided with a power source switch for the apparatus 1, an ammeter for monitoring the amount of current consumed by the apparatus 1, and the like. The computer 12 is provided with a keyboard 14 from which instructions are given to the apparatus 1, a CRT display device 15 for displaying subsidiary information related to the instructions given to the apparatus 1, data from the analysis of a liquid sample and for displaying other items, a printer 16 for printing out data obtained from the analysis of a liquid sample, and a floppy disk drive unit 17 for accommodating a floppy disk which stores commands, with which various instructions are given to the apparatus 1, and data obtained from the analysis of a liquid sample.

Figure 2:
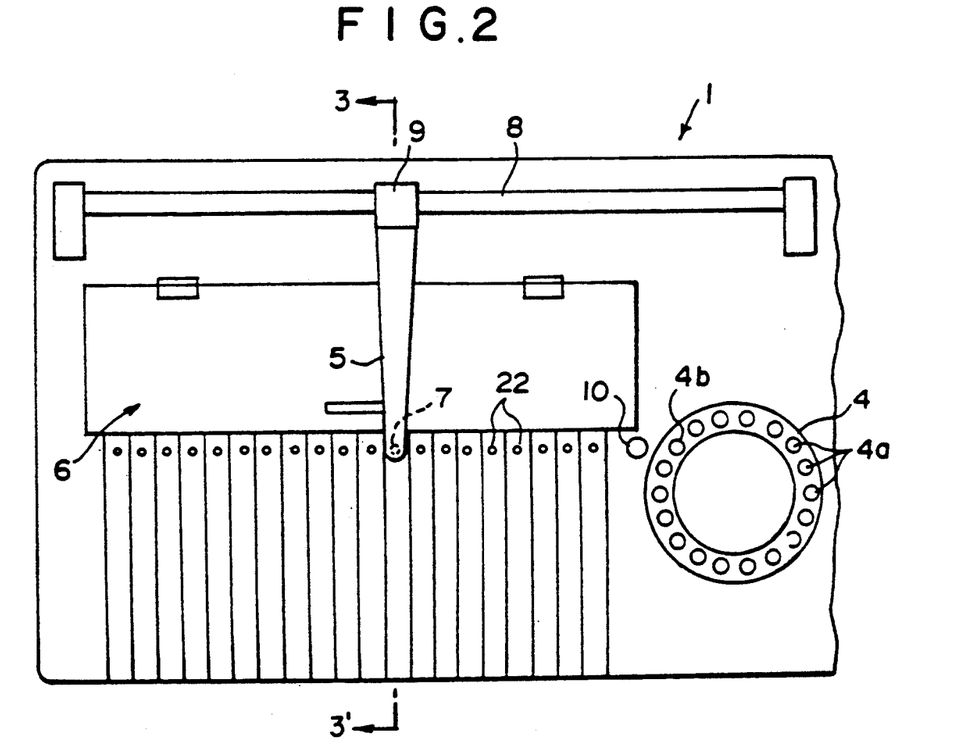
FIG. 2 is a plan view showing the major part of the biochemical analysis apparatus shown in FIG. 1.

With reference to FIG. 2, which shows a major part of the apparatus 1, the test film accommodating means 6 is constituted so that an imaginary line connecting the sample applying positions 22 for all of the long test films 3 is straight. Also, the nozzle washing area 10, and a liquid sample take-out position 4b in the sample accommodating means 4 are disposed on said imaginary line.

The sample accommodating means 4 accommodates a plurality of liquid samples in accommodating regions 4a, which are in the ring-like structure. The accommodating regions 4a are automatically rotated by a rotation means (not shown) until the liquid sample which is accommodated in one of the accommodating regions 4a and is to be used in the next analysis arrives at the take-out position 4b. In order to prevent the liquid samples accommodated in the accommodating regions 4a from evaporating and deteriorating, a cover (not shown) is provided on the accommodating regions 4a. A break in the cover exists at the take-out position 4b.

The sample application arm 5 is moved by the movement means 9 along the rail 8, takes up the liquid sample from the take-out position 4b, and applies it to a sample applying position 22 on the long test film.

Figure 3:
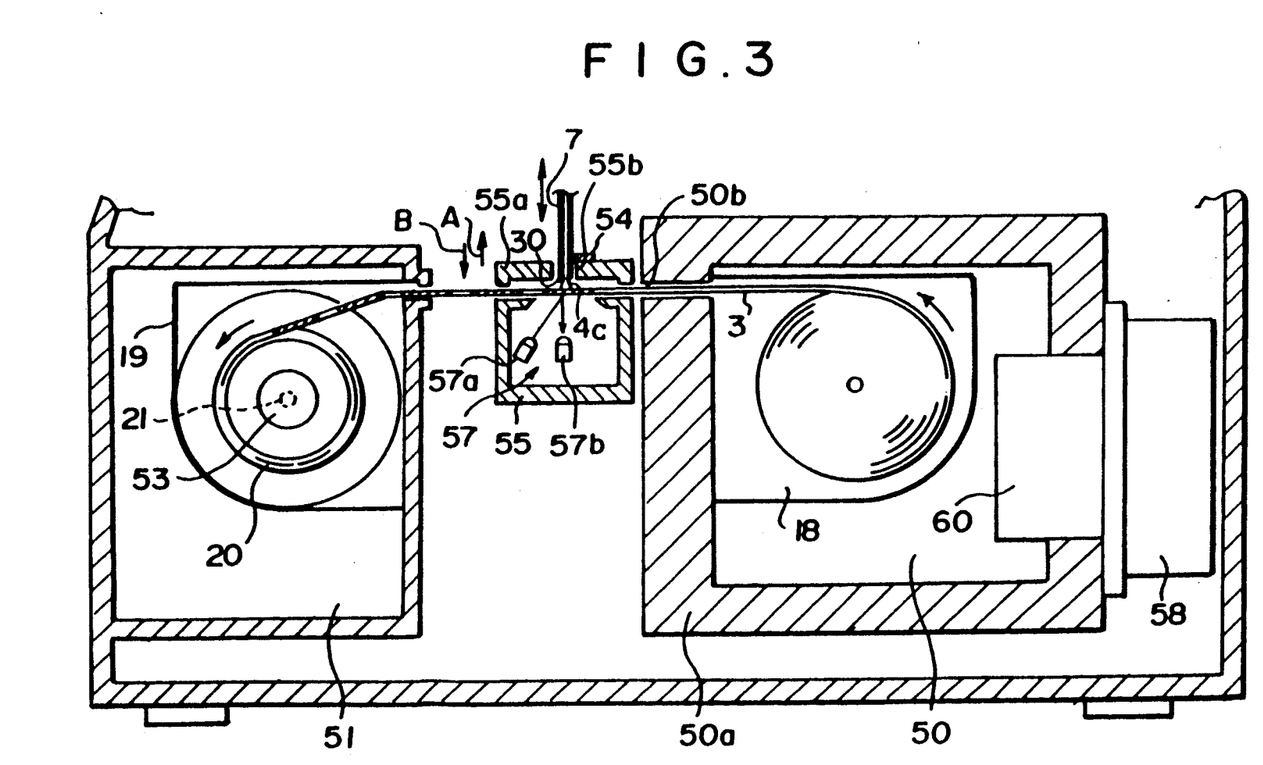
FIG. 3 is a schematic view showing the major part of the cross-sectional configuration taken along line 3—3 of FIG. 2.

FIG. 3 shows the sectional configuration taken along line 3—3 of FIG. 2. In FIG. 3, similar elements are numbered with the same reference numerals with respect to FIGS. 1 and 2.

With reference to FIG. 3, a long test film 3 is accommodated in the film feed cassette 18 and the film wind-up cassette 19 and is fed into the test film accommodating means. Specifically, the film feed cassette 18 is accommodated in a refrigerator 50 in which the temperature is adjusted to 4° C., by way of example, and the film wind-up cassette 19 is accommodated in a wind-up chamber 51. Accordingly, in this apparatus, a supporting means which supports the long test film 3 at a predetermined sample applying position is constituted of a support for the film feed cassette 18 in the refrigerator 50 and a support for the film wind-up cassette 19 in the wind-up chamber 51. Because the unused portion of the long test film 3 is accommodated in the film feed cassette 18, it can be accommodated in the refrigerator 50 without the hands of an operator contacting it. The refrigerator 50 is enclosed by a refrigerator wall 50a composed of a heat insulating material. A cooling and dehumidifying device 58 which keeps the inside of the refrigerator 50 at a predetermined low temperature and humidity is provided on one surface of the refrigerator wall 50a, and air inside the refrigerator 50 is circulated by a fan 60.

A rotation shaft of a wind-up motor 53, which acts as a conveyance means for the long test film 3, winds the long test film 3 around the reel 20 of the film wind-up cassette 19 by engaging the hole 21 formed at the center of the reel 20. As the motor 53 rotates, the long test film 3 is pulled out of the film feed cassette 18 through a film outlet 50b of the refrigerator 50, and is wound up in the film wind-up cassette 19.

Because a used long test film 3 is accommodated in the film wind-up cassette 19, it can be taken out of the apparatus 1 and discarded or processed for other purposes without the hands of an operator contacting it.

Instead of the used film being wound up in the film wind-up cassette 19, the film wind-up cassette 19 may be omitted, and a box for receiving the film may be provided in the wind up chamber 51. The box is capable of being inserted into and removed from the apparatus 1. A cutter for cutting the used film may be provided near the inlet of the region of the wind-up chamber 51, and the used film may be cut and stored in the box. With this configuration, when the used film stored in the box is to be taken out of the apparatus 1, the box can be removed, and the used film may be discarded or processed for other purposes without the hands of an operator contacting it. In this case, the test film may be pulled from the film feed cassette 18 by conveying rollers which grasp and convey the test film.

An incubator 55 in which the long test film 3 incubates and through which the long test film 3 then passes is provided between the film feed cassette 18 and the film wind-up cassette 19. A density measuring device 57 is provided in the incubator 55. The density measuring device 57 finds the optical density which depends on how much of a reaction product was formed from the reaction between the liquid sample and the reagent in the long test film 3.

The long test film 3 is intermittently pulled out of the refrigerator 50 by the motor 53, and intermittently fed leftward in FIG. 3. Prior to this step, an upper cover 55a of the incubator 55 is moved up in the direction indicated by the arrow A. After the long test film 3 is moved forward (to the left in FIG. 3), the upper cover 55a is moved down in the direction indicated by the arrow B. The downward action of the upper cover 55a pushes down the long test film 3. Then, a shutter 54 covering a hole 55b in the upper cover 55a through which the sample applying nozzle 7 is to be inserted is moved rightward, and as illustrated the sample applying nozzle 7 is moved down from its retracted position above the incubator 55 to the sample applying position at which the sample applying nozzle 7 applies a liquid sample to the long test film 3 through the hole 55b. Before being moved down to the sample applying position, the sample applying nozzle 7 delivers the liquid sample until a droplet 4c of the liquid sample forms at the leading edge. When the sample applying nozzle 7 is located at the sample applying position, the droplet 4c comes into contact with the long test film 3 as illustrated and thus is applied thereto. Thereafter, the sample applying nozzle 7 is moved up to its retracted position, and the shutter 54 is moved leftward and covers the hole 55b, which prevents air from flowing between the inside and outside of the incubator 55. Accordingly, the temperature in the incubator 55 is kept at a predetermined level, for example, 37° C. The film portion, to which the liquid sample has been applied and over which it has spread, is indicated by the hatching in FIG. 3 and is incubated for a predetermined time (four minutes, for example) in the incubator 55. In the course of the incubation or after the incubation is finished, the optical density of the portion of the long test film 3, to which the liquid sample has already been applied, is found with the density measuring device 57. The density is found by a process wherein light produced by a light irradiation means 57a, which light has a wavelength which is selected in advance, is irradiated onto the long test film 3, and the light reflected by the long test film 3 is detected by use of a photodetector 57b.

Application of the next liquid sample becomes possible after the application, incubation and analysis of a previously applied liquid sample are completed in the manner described above. The long test film 3 remains inside the incubator 55 after the analysis of the most recently applied liquid sample is finished, and is moved just prior to the application of the next sample to be analyzed so that the film portion which is to be used for the next analysis is brought to the sample applying position.

As described above, a plurality of long test films 3 containing different reagents are accommodated in the test film accommodating means 6. The thickness of the long test films 3 differs depending on the kinds of reagents contained therein. Also, the dimensional accuracy of the apparatus along the direction in which the long test films 3 are located side by side cannot easily be made constant, and therefore the height at which the long test films 3 are supported varies slightly among the positions (channels) at which the long test films 3 are located. Therefore, if the sample applying nozzle 7 were moved down a constant distance from its retracted position when applying liquid samples to the long test films 3 the liquid samples could not be applied accurately. In this apparatus, in order to eliminate this problem, a test film sensor 30 is provided at the leading edge of the sample applying nozzle 7. Before the droplet of a liquid sample forms at the leading edge of the sample applying nozzle 7 and is applied to a long test film 3, the test film sensor 30 detects the position (height) of the surface of the long test film 3. When a droplet of a liquid sample is applied to a long test film 3, the distance by which the sample applying nozzle 7 is moved down is adjusted in accordance with the detected height of the surface of the long test film 3. How the sample applying position of the sample applying nozzle 7 is controlled will be described hereinbelow with reference to FIGS. 4, 5 and 6.

Figure 4:
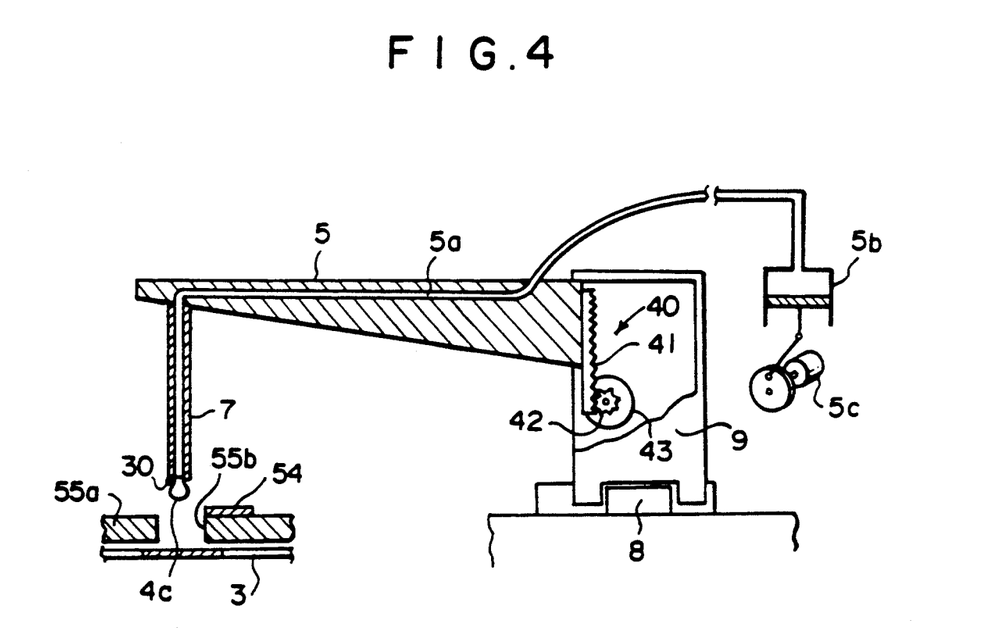
FIG. 4 is a cross-sectional view showing the part of the biochemical analysis apparatus shown in FIG. 1 in the vicinity of the sample applying nozzle.

With reference to FIG. 4, a tube 5a extending through the sample applying nozzle 7 and the sample application arm 5 communicates with a cylinder 5b. The operation of a motor 5c results in an increase or reduction in the amount of air in the cylinder 5b, and a liquid sample is thereby taken up into the sample applying nozzle 7 or delivered out of the sample applying nozzle 7 (i.e. the droplet 4c is caused to form at the leading edge of the sample applying nozzle 7). A vertical movement means 40 is provided in the movement means 9 and moves the sample applying nozzle 7 up and down. The vertical movement means 40 is composed of a rack 41 secured to an edge of the sample application arm 5, a pinion 42 engaged with the rack 41, and a motor 43 which rotates the pinion 42. When the motor 43 is operated, the pinion 42 is rotated and moves the rack 41 up and down, which thereby moves the sample application arm 5 up and down. In this manner, the sample applying nozzle 7 is moved to its retracted position above the incubator 55, the sample applying position, or the position at which the test film sensor 30 is in contact with a long test film 3.

As the test film sensor 30, various kinds of sensors can be used such as a photosensor, pressure sensor and electrostatic capacity sensor. Further, though in the embodiment as shown in FIG. 4 the test film sensor 30 is provided at the leading edge of the sample applying nozzle 7, it should be noted that the position of the test film sensor 30 is not limited thereto. For example, when a strain gage is used as the pressure sensor, it may be provided at an intermediate position of the sample applying nozzle 7 to detect the pressure at the leading edge. Alternatively, it may not be provided directly on the nozzle 7 but may be provided on the side of the sample application arm 5 with which the base portion of the nozzle 7 contacts. It would be noted that the invention includes the embodiment wherein the sensor 30 is provided on the side of the sample application arm.

Figure 5:
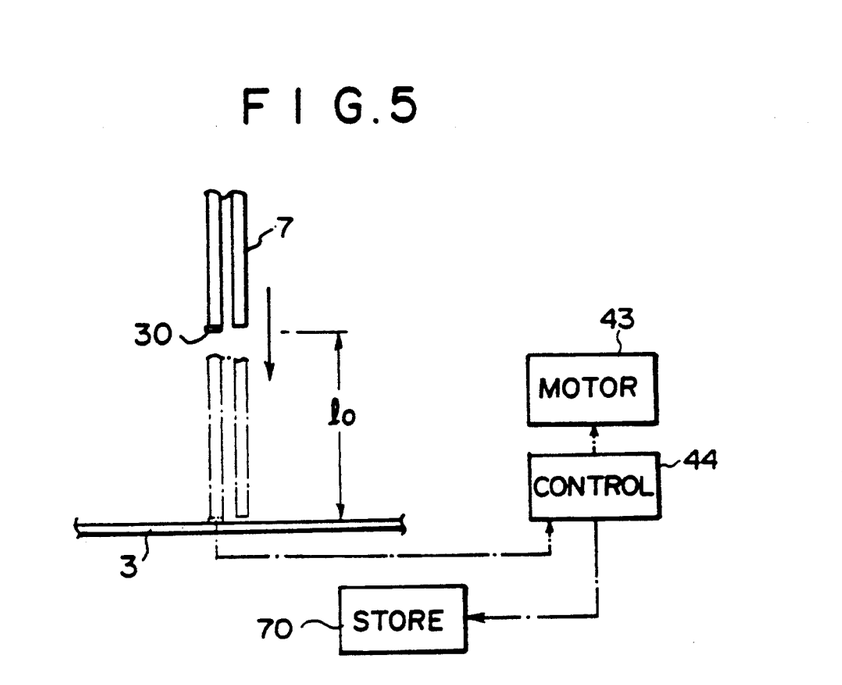
FIG. 5 is a schematic view showing the movement of the sample applying nozzle when the position of the long test film is detected.

As shown in FIG. 5, when the position of the surface of a long test film 3, to which surface a liquid sample is to be applied, is detected prior to the application of a sample, the sample applying nozzle 7 is gradually moved down from its predetermined retracted position which is indicated by the solid line. When the sample applying nozzle 7 arrives at the position indicated by the chained line, the test film sensor 30 comes into contact with the long test film 3 and generates a detection signal. The detection signal is fed to a control circuit 44 for the motor 43 of the vertical movement means 40. Upon receiving the detection signal, the control circuit 44 stops the motor 43. Also, from the extent to which the motor 43 rotated, the control circuit 44 finds the distance $l_0$ by which the sample applying nozzle 7 was moved down. The distance $l_0$ is stored in a storage means 70. By way of example, the control circuit 44 and the storage means 70 may be incorporated in the electronic processing circuit means 11 and the computer 12 shown in FIG. 1. Also, by way of example, before the apparatus is used for an analysis or a series of analyses, the positions of all the long test films 3 accommodated in the test film accommodating means 6 are detected, and information about the detected positions and information about channels where corresponding long test films 3 are located are stored in the storage means 70.

Figure 6:
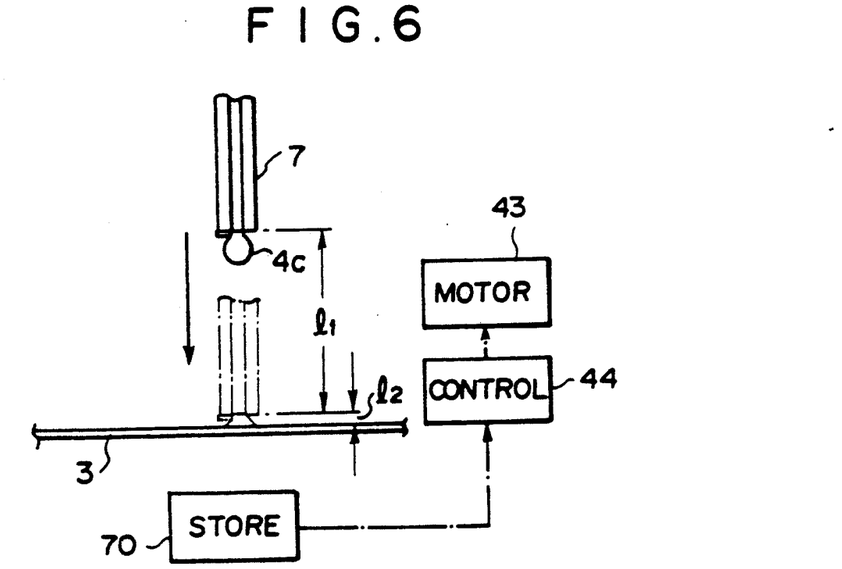
FIG. 6 is a schematic view showing the movement of the sample applying nozzle when a liquid sample is applied to the long test film.

On the other hand, as shown in FIG. 6, when a liquid sample is applied to a long test film 3, the liquid sample is delivered from the sample applying nozzle 7, which is located at its predetermined retracted position until a droplet of the liquid sample forms at the leading edge of the sample applying nozzle 7. Also, information about the channel where the long test film 3 to which the liquid sample is to be applied, a signal generated by a detection means which detects the channel above which the sample application arm 5 is currently located, and the like are fed into the storage means 70. The storage means 70 feeds a signal, which represents the distance $l_0$ found for the long test film 3 to which the liquid sample is to be applied, to the control circuit 44. The control circuit 44 calculates the distance $l_1$ by which the sample applying nozzle 7 is to be moved down during the application of a sample, from the distance $l_0$ so that the distance $l_2$ between the leading edge of the sample applying nozzle 7 located at the sample applying position and the surface of the long test film 3 is kept constant. The control circuit 44 operates the motor 43, which moves the sample applying nozzle 7 down by the distance $l_1$. Therefore, regardless of the position of the surface of the long test film 3, the sample applying nozzle 7 can be moved down to a position spaced a constant distance $l_2$ from the surface of the long test film 3, at which position the droplet 4c can be brought into contact with the surface of the long test film 3 and applied thereto with the aid of surface tension. In cases where the desired distance $l_2$ varies depending on the kinds of liquid samples or the like, the distance $l_2$ may be adjusted in accordance with the kind of liquid sample taken into the sample applying nozzle 7, or the like.

As described above, the positions of all long test films 3 accommodated in the test film accommodating means 6 are detected before the apparatus is used for an analysis or a series of analyses. When some of the long test films 3 are replaced by different kinds of new long test films, only the positions of the new long test films need be detected, and information about the detected positions may be updated. Alternatively, the position of each long test film may be detected before each application of a liquid sample to each long test film.

The dimensions of the long test film employed in the above described embodiment are preferably 3~20 mm in width and 1~10 m in length.

The device for applying liquid samples in accordance with the present invention is not limited to the type wherein a plurality of long test films are supported, and is applicable when only a single long test film is supported and a different kind of long test film later replaces the previous long test film. In such cases, the position of each long test film may be detected each time a different kind of long test film is substituted for the previous long test film. The method and apparatus for applying liquid samples in accordance with the present invention are also applicable to biochemical analysis apparatuses using chemical analysis slides.

I claim:

1. In a method for applying liquid samples in which a liquid sample accommodated in a sample applying nozzle is delivered therefrom until a droplet of the liquid sample forms at the leading edge of the sample applying nozzle, the sample applying nozzle is then moved down to a sample applying position slightly above a test film, which contains a reagent which will react with the liquid sample and give rise to a change in optical density, so that the droplet comes into contact with the test film and is applied thereto, wherein the improvement comprises the steps of:
moving said sample applying nozzle with a test film sensor down prior to the formation and application of the droplet of said liquid sample,
sensing said test film with said test film sensor,
measuring said distance by which said sample applying nozzle has been moved down;
stopping said moving of said sample applying nozzle when said test film sensor detects said test film,
storing the distance by which said sample applying nozzle was moved down, and
at the time said liquid sample is applied to said test film, adjusting the distance by which said sample applying nozzle is moved down in accordance with said stored distance so that said sample applying nozzle is moved down to a sample applying position spaced a predetermined distance from said test film.

2. A method as defined in claim 1 wherein said test film is an elongated tape test film.

3. A method as defined in claim 1 wherein said test film is a dry chemical analysis slide.

* * * * *